United States Patent
Nichols et al.

(10) Patent No.: US 8,067,655 B2
(45) Date of Patent: *Nov. 29, 2011

(54) DIISOBUTYLENE PROCESS

(75) Inventors: Natalie C. M. B. Nichols, Houston, TX (US); Christopher P. Renaudo, Houston, TX (US); David W. Leyshon, West Chester, PA (US)

(73) Assignee: Lyondell Chemical Technology, L.P., Houston, TX (US)

( * ) Notice: Subject to any disclaimer, the term of this patent is extended or adjusted under 35 U.S.C. 154(b) by 653 days.

This patent is subject to a terminal disclaimer.

(21) Appl. No.: 12/156,004

(22) Filed: May 29, 2008

(65) Prior Publication Data
US 2009/0299117 A1    Dec. 3, 2009

(51) Int. Cl.
*C07C 5/00* (2006.01)

(52) U.S. Cl. ........ 585/639; 585/255; 585/310; 585/316; 585/324; 585/329; 585/515; 585/520; 585/521; 585/526

(58) Field of Classification Search .................. 585/255, 585/310, 316, 324, 329, 510, 515, 520, 521, 585/526, 639
See application file for complete search history.

(56) References Cited

U.S. PATENT DOCUMENTS

| | | | |
|---|---|---|---|
| 3,351,635 A | 11/1967 | Kollar | |
| 3,510,538 A | 5/1970 | Rosenthal | |
| 4,100,220 A | 7/1978 | Bowman et al. | |
| 4,155,945 A | 5/1979 | Levine | |
| 4,165,343 A | 8/1979 | Levine et al. | |
| 4,447,668 A | 5/1984 | Smith, Jr. et al. | |
| 4,559,108 A | 12/1985 | Ahlberg | |
| 5,625,109 A | 4/1997 | Gupta | |
| 5,877,372 A | 3/1999 | Evans et al. | |
| 6,376,731 B1 | 4/2002 | Evans et al. | |
| 6,863,778 B2 | 3/2005 | Wang et al. | |
| 7,012,167 B2 * | 3/2006 | Kahn | 585/324 |
| 2004/0006252 A1 * | 1/2004 | Smith, Jr. | 585/639 |

FOREIGN PATENT DOCUMENTS
WO    WO 2004/080931    9/2004

* cited by examiner

*Primary Examiner* — Prem C Singh

(57) ABSTRACT

This invention is a process for producing diisobutylene from isobutylene. The process comprises first contacting a sulfonic acid resin with a reaction feed comprising isobutylene and tertiary butyl alcohol to produce a product stream comprising diisobutylene, isobutylene, tertiary butyl alcohol, and water. The product stream is distilled to produce a first overhead stream comprising water and isobutylene and a first bottoms stream comprising diisobutylene and tertiary butyl alcohol. Water is separated from the first overhead stream, and the resulting isobutylene-enriched stream is recycled back to the reaction step. The first bottoms stream is distilled to produce a second overhead stream comprising tertiary butyl alcohol and a bottoms product stream comprising diisobutylene.

7 Claims, 2 Drawing Sheets

1

DIISOBUTYLENE PROCESS

FIELD OF THE INVENTION

This invention relates to a process for producing diisobutylene from isobutylene.

BACKGROUND OF THE INVENTION

The oligomerization of olefins such as isobutylene using a sulfonic acid-type ion exchange resin catalyst is well-known in the art. For instance, U.S. Pat. No. 4,100,220 describes isobutylene oligomerization using a sulfonic acid resin catalyst and tertiary butyl alcohol (TBA) selectivity enhancing modifier to produce diisobutylene (DIB). In addition, U.S. Pat. No. 4,447,668 discloses isobutylene oligomerization using sulfonic acid resin catalyst A-15 with methyl t-butyl ether as solvent. U.S. Pat. No. 5,877,372 describes the selective oligomerization of isobutylene using a sulfonic acid resin catalyst, TBA selectivity enhancing modifier and isooctane diluent. U.S. Pat. No. 6,376,731 further discloses the oligomerization of isobutylene in the presence of a $C_3$-$C_4$ alkane diluent to enhance oligomerization selectivity and TBA to promote selectivity to DIB.

The DIB product may be used as such or may be hydrogenated to isooctane as described in U.S. Pat. Nos. 5,877,372 and 6,376,731. DIB and isooctane are potential fuel blending compositions.

In the production of DIB, it is found that minimization of water is essential to reduce detrimental unit corrosion and catalyst deactivation. However, water is often fed to the reaction section as a reactant impurity. Water is also produced by the dehydration of co-fed TBA. Because isobutylene and/or TBA streams may be recycled back to the reaction section, water can accumulate within the process such that unwanted corrosion or catalyst deactivation may occur.

Previous processes have been taught to purify DIB product. However, none of these processes have effectively dealt with the detrimental effects of water. U.S. Pat. No. 6,863,778 teaches a process to separate DIB from TBA using two distillation columns. DIB is removed as bottoms from the first distillation column and unreacted $C_4$'s are removed as overheads. A side draw containing a DIB/TBA azeotrope is fed to the second distillation column and TBA is recovered as bottoms and recycled to the reactor. However, in processes using side draws, the inventors have found that water and TBA distribute between the overhead distillate and the side draw. Water is extremely difficult to remove from either stream since water and TBA are mutually soluble. Thus, the presence of at least 1 weight percent TBA in these streams makes water soluble enough that it cannot be removed with a simple decantation step.

U.S. Pat. No. 4,559,108 also teaches a two distillation column purification of a $C_4$ hydrocarbon feed to produce a purified isobutylene stream and a high boiling component stream comprising tertiary butyl alcohol and diisobutylene. However, the TBA and DIB were not separated and there is no mention of water in the process.

In sum, new methods to produce diisobutylene by oligomerization of isobutylene over a sulfonic acid-type ion exchange resin catalyst are needed. Particularly needed are processes which limit the amount of water in the oligomerization reactor.

SUMMARY OF THE INVENTION

This invention is a process for producing diisobutylene. The process comprises first contacting a sulfonic acid resin with a reaction feed comprising isobutylene and tertiary butyl alcohol to produce a product stream comprising diisobutylene, isobutylene, tertiary butyl alcohol, and water. The product stream is distilled to produce a first overhead stream comprising water and isobutylene and a first bottoms stream comprising diisobutylene and tertiary butyl alcohol. Water is separated from the first overhead stream, and the resulting isobutylene-enriched stream is recycled back to the reaction step. The first bottoms stream is distilled to produce a bottoms product stream comprising diisobutylene and a second overhead stream comprising tertiary butyl alcohol and diisobutylene.

DETAILED DESCRIPTION OF THE INVENTION

Figure 1:
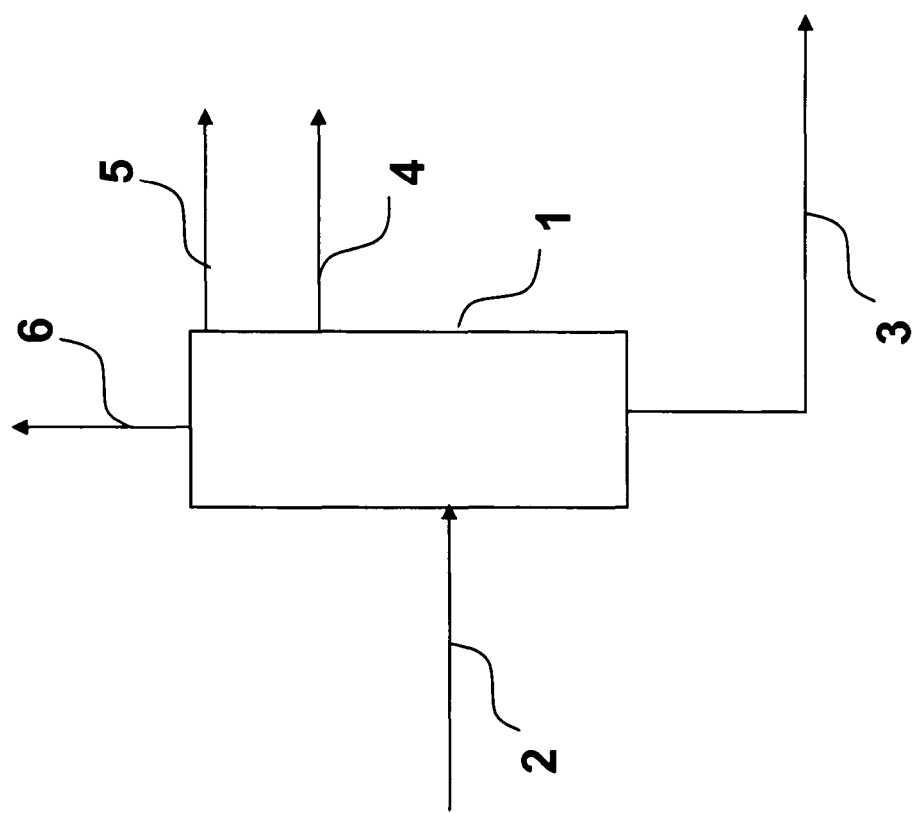
FIG. 1 is a schematic flow diagram of a single distillation tower with a side draw according to the prior art.

The process of the invention first comprises oligomerizing isobutylene to produce diisobutylene. The reaction step of the process comprises first contacting a sulfonic acid resin with a reaction feed comprising isobutylene and tertiary butyl alcohol. Sulfonic acid resin catalysts are well known. Commercial examples of sulfonic acid resin catalysts include Amberlyst A-15, Amberlyst A-35, Dowex 50, Duolite C20, Lewatit K2431, Purolite CT175, Purolite CT275, and the like. The oligomerization of isobutylene using sulfonic acid resin catalysts is well known in the art and has been described in U.S. Pat. Nos. 4,100,220, 4,447,668, 5,877,372, and 6,376,731, the teachings of which are hereby incorporated by reference.

If the sulfonic acid resin catalyst is supplied in its water wet form, it is preferably dried prior to isobutylene oligomerization. The drying may be performed by vacuum or by heat to remove the water from the resin; or the resin may be contacted with a gas or a solvent to remove the water; or the resin may be dried by first contacting the wet resin with isobutylene under conditions effective to produce tertiary butyl alcohol by reaction of isobutylene and water. Suitable conditions include temperatures in the range 35° C. to 100° C., preferably 40° C. to 80° C. Suitable pressures include pressures sufficient to maintain the liquid phase, preferably above 50 psig (0.45 MPa), most preferably from 50 to 500 psig (0.45 to 3.55 MPa). The reaction of water and isobutylene effectively dries the wet sulfonic acid resin by producing tertiary butyl alcohol which is removed from the reactor with the product stream.

If water wet resin is used in the reaction, the drying step is preferably performed in the reactor vessel such that the drying and oligomerization steps are performed in a continuous stepwise manner in the same reactor vessel. If the resin is dried by first contacting the wet resin with isobutylene, the reaction feed is preferably used for both drying and oligomerization. The drying step may also be performed in a separate vessel and then the dry sulfonic acid resin transported to a reactor vessel for the oligomerization step.

The reaction feed may include any source of isobutylene, including Cat B-B (sometimes known as Refinery B-B), raffinate streams, and isobutylene produced by the dehydration of tertiary butyl alcohol as described in U.S. Pat. Nos. 5,625,109, 3,510,538, 4,165,343, and 4,155,945. Preferably, the isobutylene is produced by the dehydration of tertiary butyl alcohol. The production of tertiary butyl alcohol by means of the Oxirane process is well known and widely practiced on an industrial scale. See, for example, U.S. Pat. No. 3,351,635.

Tertiary butyl alcohol is contained in the first reaction feed as a selectivity enhancing modifier for isobutylene oligomerization. The use of tertiary butyl alcohol in isobutylene oligomerization is taught in U.S. Pat. Nos. 4,100,220, 5,877,372, and 6,376,731. Preferably, the reaction feed contains at least 1 weight percent tertiary butyl alcohol, more preferably from 2 to 10 weight percent tertiary butyl alcohol, and most preferably from 3 to 8 weight percent.

The reaction feed preferably contains a diluent in addition to isobutylene and tertiary butyl alcohol. Diluents are believed to enhance oligomerization selectivity by reducing isobutylene concentration, and to aid in removal of the reaction exotherm. Preferably, the diluent is a $C_3$-$C_{10}$ hydrocarbon, more preferably a $C_8$ hydrocarbon in particular isooctane or diisobutylene. Most preferably, the diluent is diisobutylene. The use of alkane diluents in isobutylene oligomerization is taught in U.S. Pat. Nos. 5,877,372 and 6,376,731. If a $C_3$-$C_{10}$ hydrocarbon diluent is used, the reaction feed will preferably contain 10 to 80 weight percent $C_3$-$C_{10}$ hydrocarbon, more preferably from 20 to 70 weight percent $C_3$-$C_{10}$ hydrocarbon, and most preferably from 30 to 60 weight percent.

Preferably, the reaction feed comprises 25 to 50 weight percent isobutylene, 3 to 8 weight percent tertiary butyl alcohol, and 30 to 60 weight percent diisobutylene.

Diisobutylene is produced by contacting the sulfonic acid resin with the reaction feed under conditions effective to oligomerize isobutylene. Generally small amounts of triisobutylene are also formed in the oligomerization reaction. Usually, less than 20% of the converted isobutylene is converted into triisobutylene coproduct. In general, known oligomerization conditions can be employed in the oligomerization step. Suitable conditions include temperatures broadly in the range 50° C. to 200° C., preferably 50° C. to 150° C. Suitable pressures include those pressures sufficient to maintain the liquid phase, preferably above 50 psig (0.45 MPa), most preferably from 50 to 500 psig (0.45 to 3.55 MPa).

The oligomerization product contains diisobutylene, unreacted isobutylene, tertiary butyl alcohol, and water. The oligomerization product may also contain organic oxygenates such as acetone, methyl ethyl ketone, isobutyraldehyde, and methyl tertiary butyl ether.

The presence of water in the reaction section has been shown to be detrimental to the process, causing corrosion and resin catalyst deactivation. Thus, the removal of water from any recycle streams that may be returned to the reaction section is an important aspect of the current invention.

The diisobutylene is purified by a two-step distillation process. First, the product stream is distilled to produce a first overhead stream comprising water and isobutylene and a first bottoms stream comprising diisobutylene and tertiary butyl alcohol. In the first distillation, preferably at least 98% of the water (more preferably, at least 99.5%) is taken overhead and preferably at least 98% (more preferably, at least 99.5%) of the tertiary butyl alcohol is removed in the first bottoms stream. Since the first bottoms stream is substantially free of water, then any tertiary butyl alcohol recycle stream will be substantially free of water.

The first distillation is preferably conducted in a distillation tower wherein the top of the tower is at 80-200 psig (0.65-1.48 MPa), and more preferably at 80-85 psig (0.65-0.69 MPa), and the bottom of the tower is preferably at 85-210 psig (0.69-1.55 MPa), and more preferably at 85-90 psig (0.69-0.72 MPa). The tower overhead temperature is preferably maintained between about 40-65° C., and more preferably at 50-55° C., and the bottoms temperature is preferably maintained between about 145-205° C., and more preferably between 165-175° C. The first distillation tower preferably has at least 10 theoretical stages, more preferably at least 20 stages, with a reflux ratio (lb reflux/lb distillate) preferably of at least 0.5, and more preferably between 0.8 to 1.2.

Following the first distillation, the first bottoms stream is distilled in a second distillation tower to produce a bottoms product stream comprising diisobutylene and a second overhead stream comprising tertiary butyl alcohol and diisobutylene. If the oligomerization product contains organic oxygenates, then the oxygenates typically end up in the second overhead stream.

The second distillation is preferably conducted in a distillation tower wherein the top of the tower is preferably at 40-70 psig (0.38-0.58 MPa), and more preferably at 50-60 psig (0.45-0.52 MPa) and the bottom is preferably at 50-80 psig (0.45-0.65 MPa), and more preferably 50-70 psig (0.45-0.58 MPa). The tower overhead temperature is preferably maintained between about 125-150° C., and more preferably between 135-145° C., and the bottoms temperature is preferably maintained between about 160-195° C., and more preferably between 170-180° C. The second distillation tower preferably has at least 10 theoretical stages, more preferably at least 20 stages, with a reflux ratio (lb reflux/lb distillate) preferably of at least 0.5, and more preferably between 0.7 to 1.1.

The first overhead stream is further processed to separate water from the isobutylene. The water is separated by any known technique to remove water from a hydrocarbon stream, for instance by adsorption with adsorbents such as molecular sieves, distillation, extraction, coalescing media, or decantation. Decantation is a particularly preferred separation method. In decantation, the first overhead stream is introduced into a decanter unit where phase separation takes place. Gravity-driven phase separation of the first overhead stream results in a heavier water phase and a lighter isobutylene phase.

Preferably, the separation is operated under conditions which are effective to provide an isobutylene layer in which at least 30 percent (and more preferably at least 50 percent) of the water is removed, and an aqueous layer containing at most negligible amounts of isobutylene. For decantation, the volume of the decanter should be sufficient to provide a suitable residence time for phase separation to occur at a specified flow rate. The residence time for the water phase and the isobutylene phase is preferably at least 1 minute, and more preferably in the range of about 4 to 10 minutes. The pressure in the decanter should be sufficient to maintain both the isobutylene and the water in liquid phase, e.g. 50 to 150 psig (0.45-1.14 MPa) depending upon the temperature. The temperature in the decanter will preferably be between about 200 to 85° C., and more preferably between about 20° to 55° C. The solubility of water in isobutylene is less at lower temperature, but this may be expensive where refrigeration is needed.

Following separation, an isobutylene-enriched stream is produced. In decantation, for instance, the decanter overheads are recovered as an isobutylene-enriched stream, and the aqueous decanter bottoms are continuously removed from the decanter through an outlet at the bottom of the decanter. The isobutylene-enriched stream is then recycled back to the reaction zone for further dimerization reaction.

Preferably, the second overhead stream comprising tertiary butyl alcohol and diisobutylene is also recycled back to reactor. The tertiary butyl alcohol/diisobutylene mixture may be recycled immediately back to reactor or held in a tank prior to recycle. Excess tertiary butyl alcohol may also be dehydrated to isobutylene.

Overall, the process of the invention allows a significant portion of the water to be removed from any possible recycle streams so that water does not build up within the reaction process.

Optionally, the diisobutylene product may be hydrogenated to isooctane. The hydrogenation step can be carried out using conventional methods. For example, the diisobutylene may be brought into contact with hydrogen in the liquid phase at moderate temperatures and pressures. Suitable reaction temperatures vary from 0° C. to 500° C., but preferably from 25° C. to 200° C. The reaction is preferably conducted at or above atmospheric pressure. The precise pressure is not critical. Typical pressures vary from 1 atmosphere to 100 atmospheres. Any suitable hydrogenation catalyst may be used, including but not limited to Raney nickel and supported nickel, palladium, and platinum catalysts. Suitable supports for nickel, palladium, and platinum include carbon, silica, alumina, diatomaceous earth, and the like. Preferably, the hydrogenation catalyst is a supported nickel catalyst. The hydrogenation may be performed in the presence or absence of a solvent. Following hydrogenation, the isooctane product can be recovered by removing the hydrogenation catalyst and the solvent (if present) in a conventional manner, to separate isooctane.

The hydrogenation reaction may be performed using any of the conventional reactor configurations known in the art for such hydrogenation processes. Continuous as well as batch procedures may be used. For example, the catalyst may be deployed in the form of a fixed bed or slurry.

The following examples merely illustrate the invention. Those skilled in the art will recognize many variations that are within the spirit of the invention and scope of the claims.

Comparison Example 1

Single Tower Distillation with Side Draw

Isobutylene is dimerized over a sulfonic acid resin catalyst in the presence of TBA and diisobutylene in accordance with the process described in U.S. Pat. No. 5,877,372. The reaction product stream, comprising diisobutylene, isobutylene, TBA, and water, is purified by a process a shown in FIG. 1. The reaction product stream is passed via line 2 to a single distillation tower with a side draw (distillation tower 1). Tower 1 contains 35 ideal stages, 11 above feed and 24 below feed. The side draw is located 7 ideal stages from the top. The pressure is 70 psig (0.58 MPa) in the overhead and 75 psig (0.62 MPa) in the bottoms. The overhead temperature is at 60° C. and the bottoms temperature is 185° C. The reflux ratio is 0.9 by weight.

The bottoms stream containing mostly purified DIB is separated via line 3. The side draw stream comprising a DIB-TBA mixture that contains water is separated via line 4. The side draw contains most of the TBA for recycle back to the isobutylene dimerization reactor. The overhead stream containing unreacted isobutylene contaminated with water is removed via line 5. A vapor vent stream is removed via line 6, containing a minor amount of unreacted isobutylene.

The flow rates of the components of the various streams (in pounds per hour) are shown in Table 1.

This example shows that the use of a single distillation tower with a side draw is ineffective for removing water from the TBA recycle stream (line 4), or from the isobutylene recycle stream (line 5).

Example 2

Dual Tower Distillation

Figure 2:
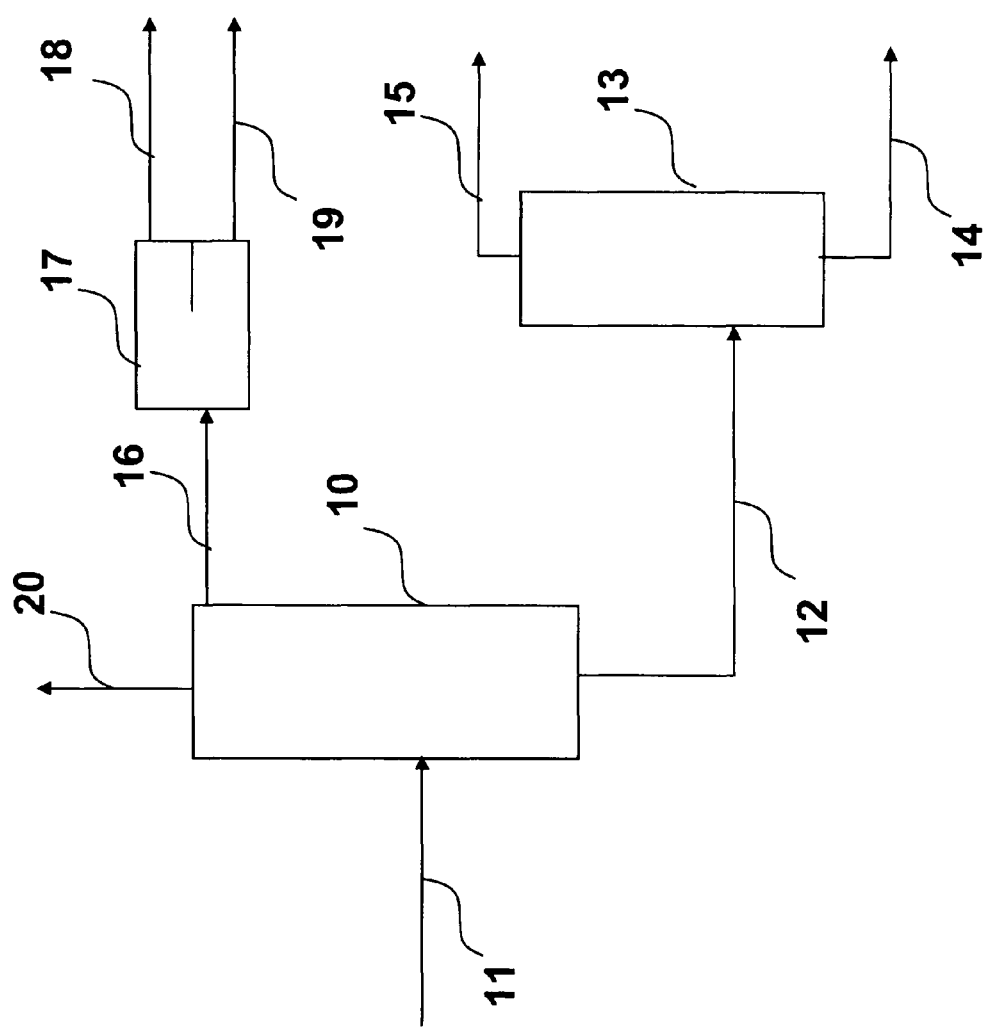
FIG. 2 is a schematic flow diagram of one embodiment of the invention.

Isobutylene is dimerized over a sulfonic acid resin catalyst in the presence of TBA and diisobutylene in accordance with the process described in U.S. Pat. No. 5,877,372. The reaction product stream, comprising diisobutylene, isobutylene, TBA, and water, is purified by a process a shown in FIG. 2. The reaction product stream is passed via line 11 to a first distillation tower 10. Tower 10 contains 35 ideal stages, 11 above feed and 24 below feed. The pressure is 85 psig (0.69 MPa) in the overhead and 90 psig (0.72 MPa) in the bottoms. The overhead temperature is 54° C. and the bottoms temp is 170° C. The reflux ratio is 0.9 by weight.

A first overhead stream is removed from the first distillation tower 10 via line 16. The first overhead stream contains most of the unreacted isobutylene and water. The first overhead stream is passed via line 16 to a decanter 17 operated at 47° C. The isobutylene and water are separated from one another by operation of the decanter to separate an isobutylene-enriched phase (stream 18) from an aqueous phase (stream 19). Stream 18 can be recycled back to the isobutylene dimerization reactor.

The first bottoms stream from distillation tower 10 is separated via line 12. The first bottoms stream comprises a DIB-TBA mixture in which all of the water and most of the unreacted isobutylene is removed. The first bottoms stream is passed via line 12 to second distillation tower 13.

Distillation tower 13 contains 21 ideal stages, 9 above feed and 12 below feed. The pressure is 55 psig (0.48 MPa) in the overhead and 58 psig (0.50 MPa) in the bottoms. The overhead temperature is 141° C. and the bottoms temp is 175° C. The reflux ratio is 0.8 by weight. The second bottoms stream from distillation tower 13 is removed via line 14. The second bottoms stream contains a purified DIB stream.

The second overhead stream is removed via line 15. The second overhead stream comprises a DIB-TBA mixture that contains no water. The second overhead stream contains most of the TBA for recycle back to the isobutylene dimerization reactor. Unlike the single distillation with a side draw, the recycle TBA stream is not contaminated with water.

A vapor vent stream is removed via line 20, containing a minor amount of unreacted isobutylene.

The flow rates of the components of the various streams (in pounds per hour) are shown in Table 2.

This example shows that the use of a dual distillation effectively removes water (via line 19) from the TBA recycle stream (line 15) and the isobutylene recycle stream (line 18).

TABLE 1

| Single Distillation with Side Draw Component Flow Rates (lb/h) | | | | | |
|---|---|---|---|---|---|
| Stream # | 2 | 3 | 4 | 5 | 6 |
| Water | 378 | 0 | 49 | 320 | 9 |
| Isobutylene | 132523 | 0 | 10059 | 119409 | 3055 |
| MEK | 6471 | 0.6 | 4100 | 2361 | 9 |
| TBA | 19738 | 0.8 | 14087 | 5630 | 21 |
| DIB | 210557 | 178973 | 30933 | 650 | 0.5 |
| TIB | 8318 | 8318 | 0 | 0 | 0 |
| Total | 377985 | 187292.4 | 59228 | 128370 | 3094.5 |

TABLE 2

| | Dual Distillation Component Flow Rates (lb/h) | | | | | | | |
|---|---|---|---|---|---|---|---|---|
| Stream # | 11 | 12 | 14 | 15 | 16 | 18 | 19 | 20 |
| Water | 378 | 0 | 0 | 0 | 353 | 117 | 236 | 24 |
| Isobutylene | 112765 | 1259 | 0 | 1258 | 108062 | 108062 | 0 | 3445 |
| MEK | 7828 | 7819 | 38 | 7781 | 10 | 10 | 0 | 0 |
| TBA | 16025 | 16007 | 16 | 15991 | 18 | 18 | 0 | 0 |
| DIB | 209727 | 209727 | 167669 | 42057 | 0 | 0 | 0 | 0 |
| TIB | 19476 | 19476 | 19476 | 0 | 0 | 0 | 0 | 0 |
| Total | 366199 | 254288 | 187199 | 67087 | 108444 | 108207 | 236 | 3469 |

We claim:

1. A process for producing diisobutylene comprising:
(a) contacting a sulfonic acid resin with a reaction feed comprising 25 to 50 weight percent isobutylene, 3 to 8 weight percent tertiary butyl alcohol, 30 to 60 weight percent diisobutylene, and 10 to 80 weight percent isooctane to produce a product stream comprising diisobutylene, isobutylene, tertiary butyl alcohol, and water;
(b) distilling the product stream to produce a first overhead stream comprising water and isobutylene and a first bottoms stream comprising diisobutylene and tertiary butyl alcohol;
(c) separating water from the first overhead stream to produce an isobutylene-enriched stream and recycling the isobutylene-enriched stream to step (a); and
(d) distilling the first bottoms stream to produce a bottoms product stream comprising diisobutylene and a second overhead stream comprising tertiary butyl alcohol and diisobutylene.

2. The process of claim 1 wherein the isobutylene is produced by the dehydration of tertiary butyl alcohol.

3. The process of claim 1 wherein the water is separated from the first overhead stream by decantation.

4. The process of claim 1 wherein at least 30 percent of the water from the first overhead stream is separated to produce the isobutylene-enriched stream.

5. The process of claim 1 wherein at least 50 percent of the water from the first overhead stream is separated to produce the isobutylene-enriched stream.

6. The process of claim 1, further comprising recycling the second overhead stream back to step (a).

7. The process of claim 1, further comprising hydrogenating the bottoms product stream to form isooctane.

\* \* \* \* \*